United States Patent [19]

Peng

[11] Patent Number: 5,289,836
[45] Date of Patent: Mar. 1, 1994

[54] DENTAL FLOSS DEVICE WITH A GUIDE POST

[76] Inventor: Chien-Lun Peng, 7F, No. 4, Alley 7, Lane 53, Sec. 4, Nanking E. Road, Taipei, Taiwan

[21] Appl. No.: 973,710

[22] Filed: Nov. 9, 1992

Related U.S. Application Data

[63] Continuation-in-part of Ser. No. 772,544, Oct. 7, 1991, abandoned.

[51] Int. Cl.$^5$ .............................................. A61C 15/00
[52] U.S. Cl. .................................... 132/329; 132/321
[58] Field of Search ................................ 132/321, 329

[56] References Cited

U.S. PATENT DOCUMENTS

| | | | |
|---|---|---|---|
| 3,896,824 | 7/1975 | Thornton | 132/321 |
| 4,011,658 | 3/1977 | Tarrson et al. | 132/329 |
| 4,064,883 | 12/1977 | Oldham | 132/321 |
| 4,326,547 | 4/1982 | Verplank | 132/89 |
| 4,364,380 | 12/1982 | Lewis | 128/89 A |
| 4,832,063 | 5/1989 | Smole | 132/329 |
| 4,974,614 | 12/1990 | Selker | 132/321 |
| 5,050,625 | 9/1991 | Siekmann | 132/323 |
| 5,094,255 | 3/1992 | Ringle | 132/321 |
| 5,183,063 | 2/1993 | Ringle et al. | 132/321 |

Primary Examiner—John J. Wilson
Assistant Examiner—Cindy A. Cherichetti
Attorney, Agent, or Firm—Bacon & Thomas

[57] ABSTRACT

A dental floss device with a guide post for removing food debris and dental plaque during orthodontic treatment. The guide post includes a guide post of a uniform small diameter and a floss bonded thereto. The guide post has a semi-spherical tip for sensing position to ease insertion of the guide post between the clearance which is formed by teeth and the orthodontic appliance. The dental floss device is formed by injection molding.

3 Claims, 5 Drawing Sheets

DENTAL FLOSS DEVICE WITH A GUIDE POST

This application is a continuation-in-part application of U.S. Ser. No. 07/772,544 filed on Oct. 7, 1991 now abandoned.

BACKGROUND OF THE INVENTION

(A) Field of the Invention

The present invention relates to a dental floss device, particulary a dental floss device with a guide post for use in flossing between teeth having a fixed orthodontic appliance extending between the teeth. This invention also relates to a method of producing such dental floss device.

(B) Description of the Prior Art

Dental floss is used to remove food debris and dental plaque on teeth by inserting between two teeth, extending to gingival sulcus, and then sweeping on teeth surface. It is an effective way to clean proximal surface between any two teeth in addition to the use of a tooth brush, and an effective tool to prevent from proximal caries and periodontities. However, in the course of orthodontic treatment, where a fixed orthodontic appliance is used, a metal wire fixed between teeth would prevent from passing through of the dental floss for cleaning of the tooth surface. There is a kind of flossing device with a hardened tip or needle-like tip for cleaning beneath fixed bridge, but its insertion to the small gap between a tooth and an orthodontic arch wire always causes injury to gums. Moreover, its tip in the form of a pin point can not provide any feeling about the depression area between teeth, and therefore a mirror should be used to find its position. It is quite inconvenient to use such dental flossing device.

Many prior art devices provide various dental floss threaders for different purposes, but most of which are intended for the use of threading floss between teeth for normal care of oral hygine. U.S. Pat. No. 5,050,625 to Siekmann, for example, discloses a threading device formed of a tube including a handle portion and a blade-like portion with a dental floss detachably retained therein. There are several disadvantages in the Siekmann disclosure. Such device with tapered blade-like portion is rendered harmful for gum tissue and is not applicable for flossing between the clearance formed between teeth and the orthondontic appliance. Moreover, each cleaning location requires a new threading device.

U.S. Pat. No. 4,326,547 to Verplank, and U.S. Pat. No. 4,011,658 to Tarrson et al disclose dental floss devices for cleaning the gap between teeth. U.S. Pat. No. 5,094,255 to Ringle discloses a dental floss device to remove plaque in the sulcus area of one's mouth. This device has a leader tapering to a point remote from the floss. The point end of such design is hurtful when not used carefully. Such device is not applicable for orthondontic patients because the diameter of the end which attaches to multiple strands of floss must be quite large. Therefore, patients under orthodontic therapy cannot feel the correct dimension of the clearance between teeth and the orthodontic arch wire simply by the aid of the point end. The correct dimension of the clearance can only be felt when the whole device has been passed through the clearance. The orthodontic appliance is likely to be pushed away from the teeth and falls off owing to an excessive force applied by the user to pull the larger diameter portion of the device through the clearance.

As to the method for producing dental floss devices, U.S. Pat. 5,094,255 to Ringle, for example, put a strand of fiber between an upper portion and a lower portion of a mould, each of the portions having corresponding peaks which form the point ends of two leaders when the mould is closed. Before injection of resin material, the mould close and the fiber will be raised. Problems thus appear as follows:

A. When the mould closes, the fiber 21 will be moved to a position away from the center of the leader portion 22 as shown in FIG. 5(a) taken from the cross section of the tapered portion of the leader. Therefore, an excessive tension will be introduced into the fiber, particularly the point tip of the leader. It is very important that the fiber be surrounded with a resin material uniform in radial thickness, and that the fiber has a certain tension optimal to keep the fiber being in a straight line. Otherwise the floss in the resin material will wind along the leader as illustrated in FIG. 5(b) and is likely to fall off due to poor bonding between the floss and the leader resulted from the contraction of the floss or the pressure induced by the stroke of injected resin material.

B. The surface where the tip of a leader is separated from the tip of another leader after ejected from the mould will be rough and therefore will cause injury to gums.

Therefore the first object of the present invention is to provide a dental floss device which has a guide post of a uniform diameter for a user to feel the dimension of the clearance between teeth and orthodontic arch wire without the help of a mirror. If the front end portion can pass through the clearance without difficulties, the tail end portion with a floss will of course pass through easily.

The second object of the present invention is to provide a dental floss device whose guide post has a unibody moulded semi-spherical tip for protective purposes to gums.

Another object of the present invention is to provide a method of producing the dental floss device which is more easier and more economical of floss than known prior arts.

SUMMARY OF THE INVENTION

The present invention is a dental floss device comprising a guide post and a floss attached thereto for the use with a fixed orthodontic appliance for the purpose of removing food debris and dental plaque on teeth, and consequently preventing from occurrence of proximal caries and periodontal disease during the treatment of orthodontics. The guide post is small in a uniform diameter which can pass through a small gap between orthodontic arch wire and teeth. Being resilient and having a semi-spherical tip, the guide post can be operated without injuring gums.

The present invention is a method for producing above mentioned dental floss device as well.

The objects discussed above and others and advantages will be made manifest when considering the following detailed specification when taken in conjunction with the appended drawings.

DETAILED DESCRIPTION OF THE PREFERRED EMBODIMENT

Figure 1:
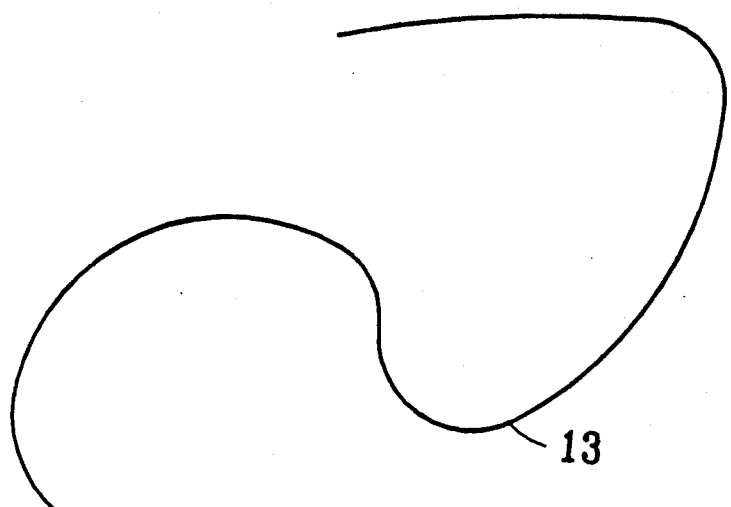
FIG. 1 is a side view of a dental floss device with a guide post for orthondontics according to the present invention.
Figure 1:
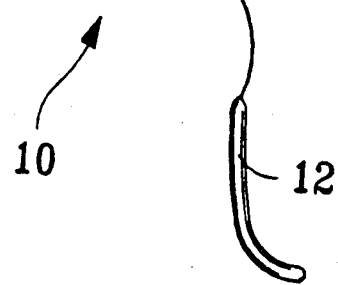
Figure 2:
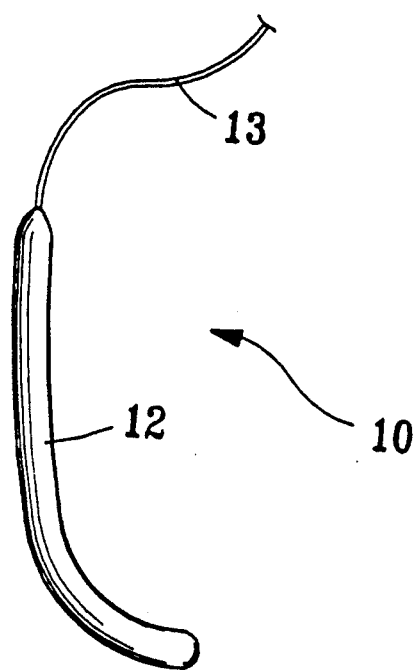
FIG. 2 is a perspective view of the dental floss device with a guide post for orthodontics according to the present invention.

Please refer to the attached as seen in FIGS. 1 and 2, the present invention provides mainly a dental floss device (10) with a guide post for orthodontics. The dental floss device (10) has a guide post (12) having a front end portion being curvilinear for guiding and for protection of gums. The guide post (12) has a semi-spherical tip to prevent from damaging the gums. It has a relatively long tail portion to facilitate holding with a hand. A floss (13) is connected to the tail end of the guide post (12). The cross-sectional diameter is uniform throughout the guide post, preferably 1 mm to 1.3 mm.

Figure 3:
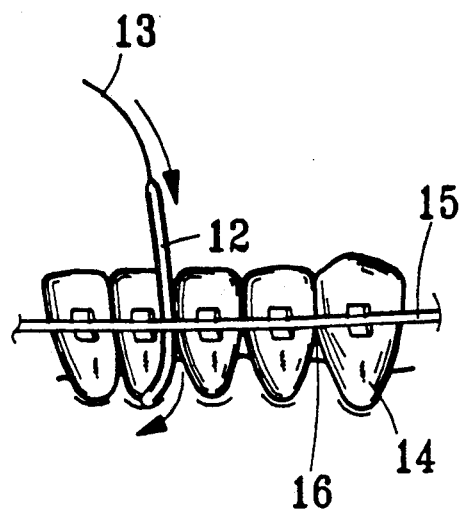
FIG. 3 is a perspective view of the dental floss device with a guide post for orthodontics at ready in guiding condition according to the present invention.
Figure 4:
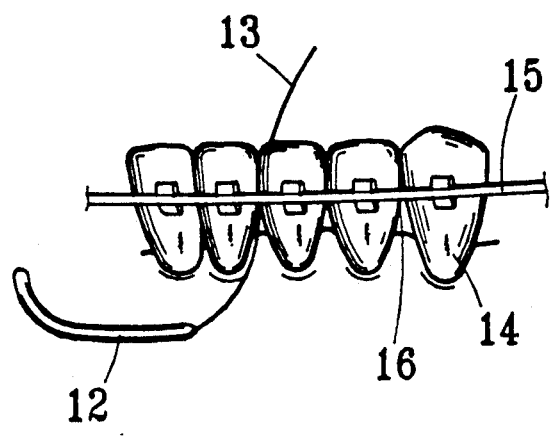
FIG. 4 is a perspective view of the dental floss deive with a guide post for orthodontics at working condition according to the present invention.
Figure 5:
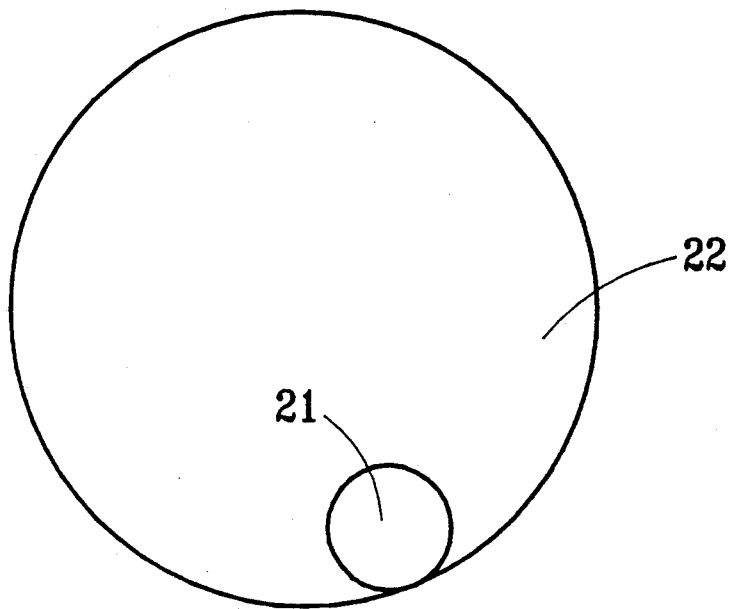
FIG. 5(a) is a cross sectional view of a leader of a flossing device produced by a prior art.
FIG. 5(b) illustrates a floss winding in a leader of a flossing device produced by a prior art.
Figure 5:
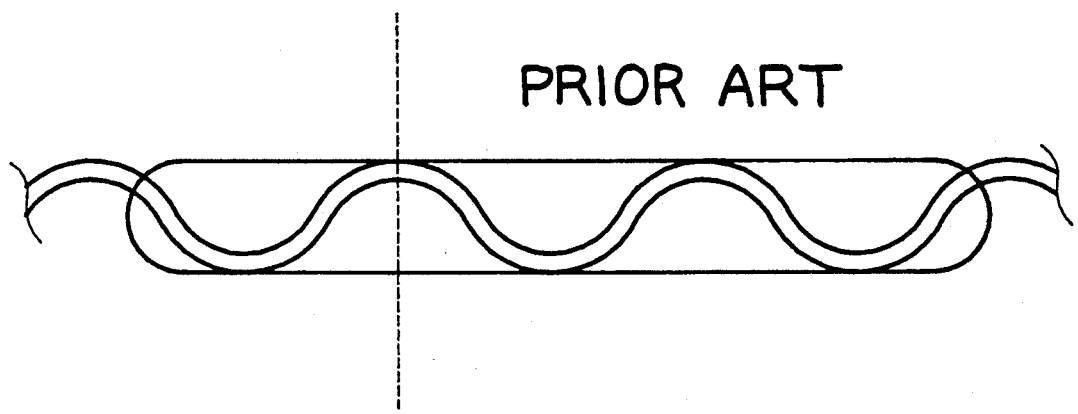

Referring to FIGS. 3 and 4, the curved guide post (12) is for inserting to a gap between teeth (14) and an orthodontic arch wire (15) so that the floss (13) can clean the proximal surface (16) on the teeth (14). When the guide post (14) is prepared to insert into the gap between teeth (14) and the orthodontic arch wire (15), the user can easily locatae the path by feeling the depression on the adjacent surface of two teeth, and keeps close contact with the adjacent surface (16), and enters the gap along a curved rotation. After entering the gap, the guide post (12) leaves the gum gradually because of its curved shape and also the rotated motion. That is a way to protect the gums. Moreover, the curved guide post (12) can be designed in a form corresponding to the physiological shape of the gums for close and safe cleaning and massage effect.

Figure 6:
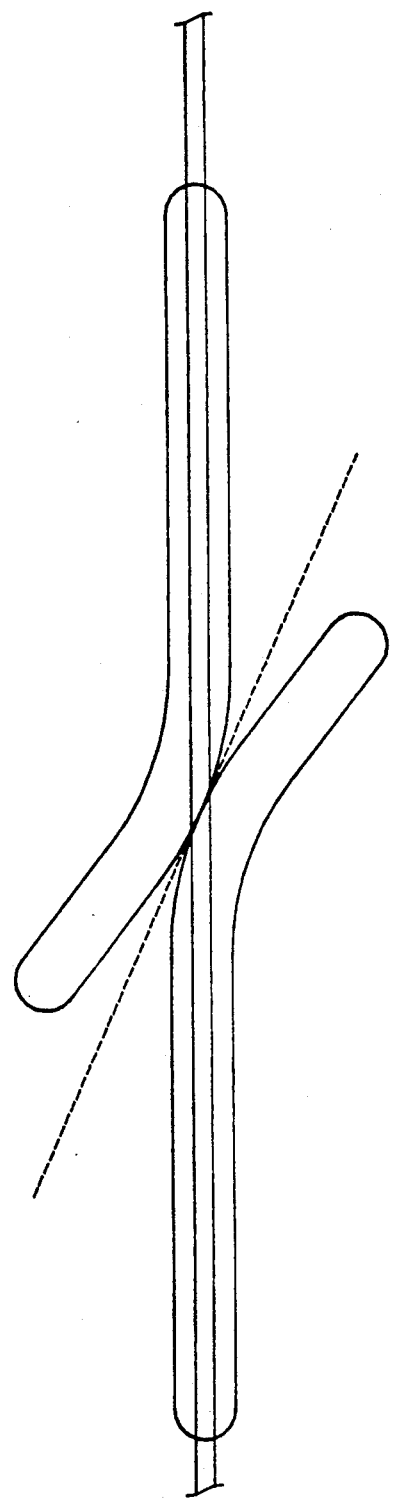
FIG. 6(a) illustrates the arrangement of the cavity taken from the parting plane of a mould according to the present invention.
FIG. 6(b) illustrates a longitudinal sectional view of a dental floss device with a guide post according to the present invention.
FIG. 6(c) is a cross sectional view of the tail end portion of the guide post of a dental floss device according to the present invention.
Figure 6:
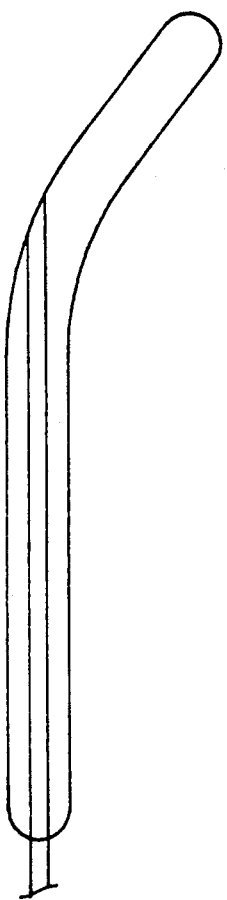
Figure 6:
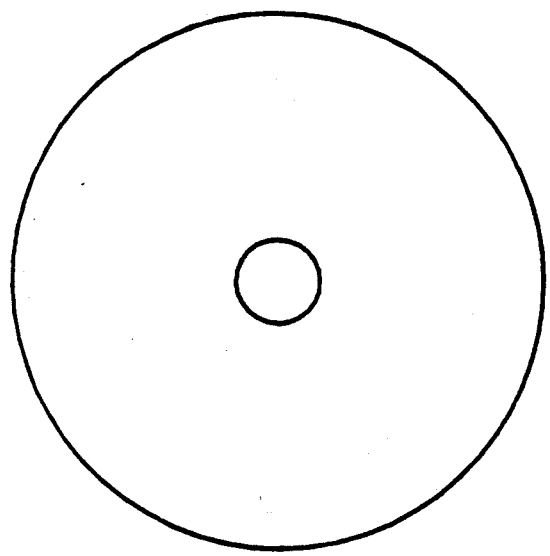

FIG. 6(a) is a view taken from the parting plane of a mould having a first mould portion and a second mould portion, in which the arrangement of the cavity for two dental floss devices is illustrated. The cavity is in a form of two parts corresponding to two guide posts. Each of the cavity parts includs a front end portion and a tail end portion. The cavity is such designed that one part is tangential to the other part at the place where each part bends, and that the two tail portions are positioned on a same line. The cavity is divided equally by the first mould portion and the second mould portion along the parting plane which is presented by the sheet of paper. A continuous floss coming along the direction of the cavity corresponding to the tail portions of two guide posts is kept straight under a certain tension. Closing the mould, injecting a resin material into the cavity through a properly positioned gate to encapsulate the floss, and separation after ejection will produce two dental floss devices each cycle. FIG. 6(b) illustrates a longitudinal sectional view of the present invention produced according to this method. The floss surrounded in the guide post is in a straight line. FIG. 6(c) is a cross-sectional view of the tail end portion of a guide post according to the present invention, in which the floss is surrounded in the center of the cross section.

As indicated, the structure and the method herein may be variously embodied. Recognizing various modifications will be apparent, the scope hereof shall be deemed to be defined by the claims set forth below.

What is claimed is:

1. A method for producing a dental floss device comprising the steps of:
   a) providing a mould having a cavity defining two guide posts, with each guide post having a tail end portion, a curvilinear front end portion terminating in a semi-spherical tip and a substantially constant diameter from the front end portion to the tail end portion, the two guide posts being tangential to each other at curvatures of the front end portions and on a parting plane of the mould, and the tail end portions extending longitudinally along a straight line;
   b) disposing a floss in the cavity; and
   c) injecting an encapsulating material into the cavity to encapsulate the floss and produce two dental floss devices, with each device including a guide post and a floss having a first end securely fixed to the tail end portion so that the entire guide post may be threaded through a gap formed between an orthodontic appliance and teeth to which the appliance is fixed to position the floss for flossing between the teeth.

2. The method of claim 1 wherein the encapsulating material is an elastomeric material.

3. The method of claim 1 wherein the floss disposed in the cavity extends longitudinally through the tail end portions of the guide posts without passing through the front end portions.

* * * * *